United States Patent [19]

Kalbitz et al.

[11] 4,251,850
[45] Feb. 17, 1981

[54] CONTROL DESK FOR MEDICAL APPARATUS, IN PARTICULAR FOR AN X-RAY DIAGNOSTIC APPARATUS

[75] Inventors: Wolfgang Kalbitz; Erwin Keyl; Walter Satzinger; Hans Wichert, all of Erlangen, Fed. Rep. of Germany

[73] Assignee: Siemens Aktiengesellschaft, Berlin & Munich, Fed. Rep. of Germany

[21] Appl. No.: 17,031

[22] Filed: Mar. 2, 1979

[30] Foreign Application Priority Data

Mar. 28, 1978 [DE] Fed. Rep. of Germany ....... 7809246

[51] Int. Cl.³ .............................................. H02B 1/04
[52] U.S. Cl. .................................... 361/331; 361/334; 361/390; 312/209; 74/577 S
[58] Field of Search ................ 340/705, 755; 312/209; 108/7; 361/331, 334, 346, 350, 358, 359, 390, 391; 74/81.19, 89.14, 577 R, 577 S, 577 M

[56] References Cited

U.S. PATENT DOCUMENTS

| | | | |
|---|---|---|---|
| 814,286 | 3/1906 | Harris | 108/7 |
| 2,566,064 | 8/1951 | Keim | 361/390 |
| 2,569,310 | 9/1951 | Hitt | 108/7 |
| 2,885,600 | 5/1959 | Wiseman | 361/390 |
| 2,933,656 | 4/1960 | Ruth | 361/334 |

OTHER PUBLICATIONS

Prospectus (Siemens), Tridoros Optimatic 800, Data, Bested Nr. MR 65/184, West Germany.

Primary Examiner—Gerald P. Tolin
Attorney, Agent, or Firm—Hill, Van Santen, Steadman, Chiara & Simpson

[57] ABSTRACT

In an exemplary embodiment, an indicator panel containing indicator elements and control switches is pivotal relative to the remainder of the control desk so as to be adjustable for optimum visibility in accordance with the position and height of the operator. The indicator panel may be held at the desired inclined position either by a pawl which can be automatically flipped over by manipulation of the panel for resetting of the panel or by means of a reversible electric drive.

13 Claims, 2 Drawing Figures

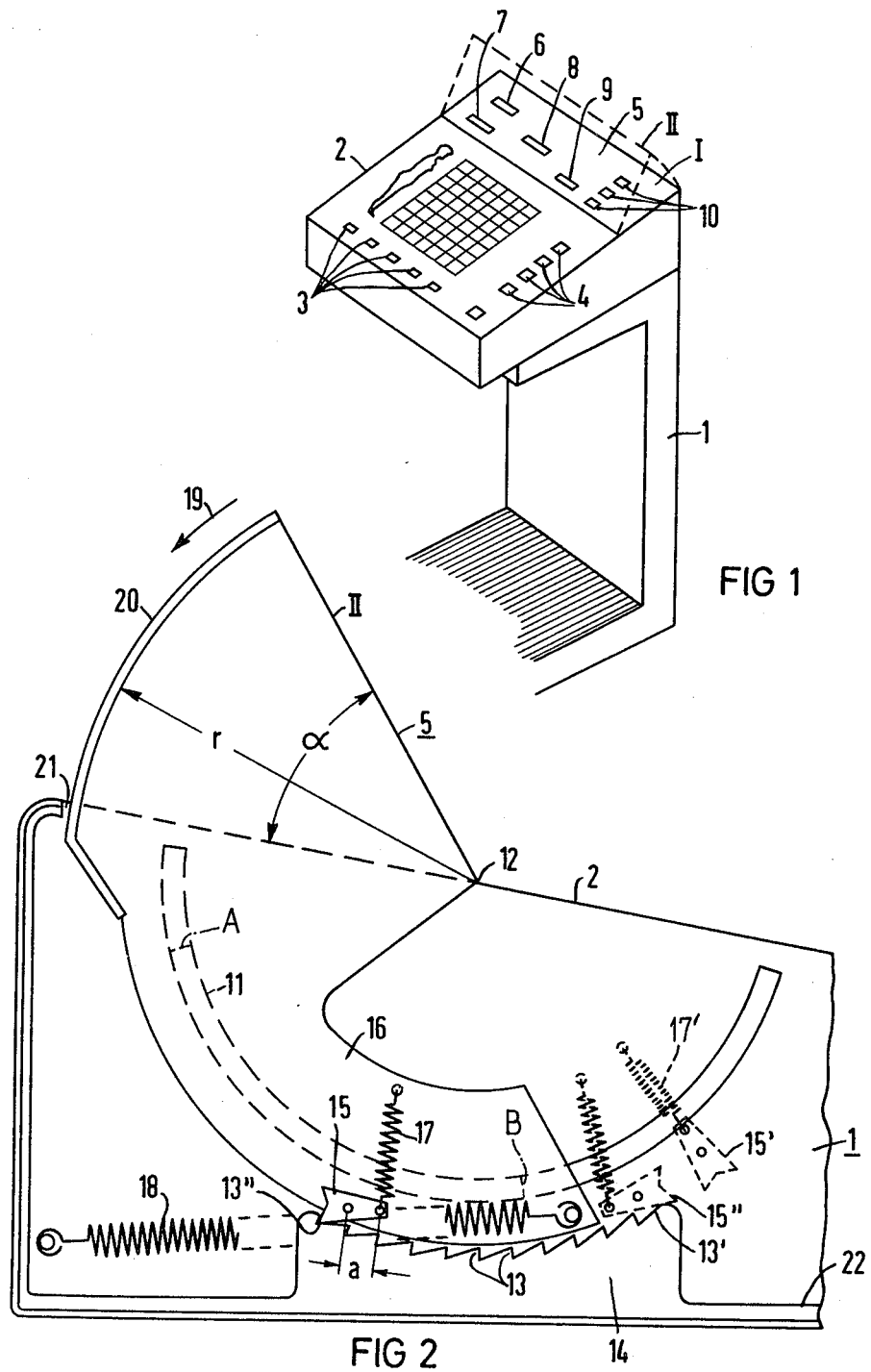

CONTROL DESK FOR MEDICAL APPARATUS, IN PARTICULAR FOR AN X-RAY DIAGNOSTIC APPARATUS

BACKGROUND OF THE INVENTION

The invention relates to a control desk for medical apparatus, in particular for an x-ray diagnostic apparatus containing indicator elements for providing optical information in addition to control elements.

For x-ray diagnostic apparatus and equipment it is known to arrange the indicator elements for displaying optical information together with the control elements such as organ keys, on and off switches, control keys, etc., on the top surface of a control desk, the surface beig arranged horizontally or slightly inclined, as a rule.

Such an arrangement does not permit, in particular when the operator is not standing directly in front of the control desk, a satisfying precise determination of the information indicated by the indicator elements. It is an objective of the invention to provide an improved readability of indicator elements in comparison to prior art control desks of this type.

SUMMARY OF THE INVENTION

The objective posed is resolved in a control desk of the initially mentioned type according to the invention in that the indicator elements are arranged on an indicator panel which is pivotably supported for movement into at least one operating position from a base position. It is thus possible for the operator to adjust the indicator elements to the location, taken up by the operator, so that the indicator elements are always in proper view for the operator.

Advantageous embodiments and further developments of the invention are contained in the subclaims. One exemplary embodiment of the invention is subsequently more precisely explained with the aid of the accompanying sheet of the drawings; and other objects, features and advantages will be apparent from this detailed disclosure and from the appended claims.

BRIEF DESCRIPTION OF THE DRAWINGS

FIG. 1 depicts a control desk according to the invention in a diagrammatic illustration; and FIG. 2 illustrates a segment of the control desk in side view.

DETAILED DESCRIPTION

FIG. 1 illustrates a control desk 1 for an x-ray diagnostic apparatus having organ-designating keys 3 arranged at the top surface 2, and also additional keys 4 with the aid of which a specific exposure system for a chosen organ can be selected and switched on, having reference to a coordinated program chart not more precisely referenced, which is arranged on the top surface 2 in association with keys 3 and 4. An indicator panel 5 is arranged on the rear side of the control desk 1, said panel containing several optical indicator elements 6 through 9 and also a line of keys 10. The indicator elements 6 through 9 indicate optical information, for example, in regard to exposure data, the set tube voltage (kV), the adjusted tube current (mA) and regarding the preselected switch-on time of the x-ray diagnostic apparatus. In addition, various indicator lamps can be present which indicate the operation and functional processes being effected by the x-ray apparatus.

The indicator panel 5 which, as illustrated, extends across the total width of control desk 1, is supported on the control desk so it can be swung out, and indeed such that it can be brought from the base position, referenced as position I, into at least one operating position referenced II and indicated by dash lines in FIG. 1.

FIG. 2 shows details of the support of the indicator panel 5 in the control desk 1. In the position drawn, the indicator panel 5 is swung out of the top surface 2 of the control desk by the acute angle $\alpha$. For mounting of the indicator panel 5, the indicator panel is supported in a guideway referenced 11, which has a center of curvature which represents the center of rotation for the indicator panel 5 at the pivot axis represented by point 12. The guideway 11 is formed by a groove in the lateral wall of the control desk. A slide ring segment conforming with the contour of the guideway 11 is fixed to a frame 16 supporting the indicator panel 5. The slide ring segment may extend along the guideway 11 over an arcuate extent corresponding to the section of guideway 11 shown with dash lines between points A and B in FIG. 2; that is over an arcuate extent of about ninety degrees (the dash lines at 11 between A and B in FIG. 2 thus also representing such slide ring segment except for the necessary mechanical clearance so that the slide ring segment can slide in the guideway 11 as panel 5 is pivoted between its respective positions as hereafter described). One or more pins can be provided for engaging in guideway 11 in place of the slide ring segment, for example at points A and B.

So the indicator panel 5 can be supported in various operating positions having different angles of tilt $\alpha$, a locking device is present which consists of a locking means 14 provided with several locking steps or teeth 13 and a locking pawl 15 which can be brought into engagement with the locking steps or teeth 13. The pawl 15 is here supported on a frame 16. A tension spring 17, hooked at the frame 16, acts at a spacing a from the pawl pivot axis, the tension spring effecting a reversal of the locking pawl 15 at the end positions. A reset spring is referenced 18 and serves to urge the total indicator panel 5 in a direction opposite to the direction of arrow 19.

In the position drawn in FIG. 2, the locking pawl 15 is engaged with the last locking tooth 13''. If the indicator panel 5 is pivoted into the base position in the direction of arrow 19, the locking pawl 15 ratchets along the locking part 14. At the end of travel in the direction of arrow 19, the locking pawl 15 assumes the radial position indicated by dash lines at 15' because of the action of the tension spring 17 (indicated at 17'). If the manual shifting pressure which has been exerted against the action of tension spring 18 is withdrawn, the spring 18 now tends to return the indicator panel 5 in a clockwise direction (as viewed in FIG. 2) relative to the top surface 2 of control desk 1. This causes the locking pawl 15 to shift into the non-ratcheting position referenced 15''. In this position the locking pawl 15 now slides across the locking teeth of the locking part 14 until past the last locking tooth 13''. In that position, the locking pawl 15 again flips into a radial position due to the force of spring 17, such radial position being analogous to the position indicated at 15'. With this radial position of the pawl, the display panel 5 can now be brought from such extreme clockwise position into a desired position of incline relative to the top surface 2 of the control desk (with ratchet retention in the attained position such as the position of maximum incline actually shown in FIG. 2).

A hood-like cover 20, with a curvature corresponding to the rotation radius r, is connected with the indicator panel 5, and serves to cover an opening 21 (which is left as the indicator panel 5 is raised) in every inclined position of the indicator panel. The cover 20 expediently also laterally adjoins the display panel so that the opening 21 is closed at the sides as at the rear of the panel 5.

The locking device shown in FIG. 2 is advantageously located at both sides of the control desk 1, and the locking means 14 is integrated into the lateral wall 22 of control desk 1 in which the guideway 11 is also arranged.

For a stepless adjustment of the indicator panel 5 it is advantageous to provide an electrically driven adjustment in place of the locking device to be manually operated. For this purpose, for example, a gear wheel segment can be provided in place of the locking teeth 13, the gear wheel segment being coupled with the gear shaft of a reversible electric motor via a suitable transmission component, for example, a worm gear.

It will be apparent that many modifications and variations may be effected without departing from the scope of the novel concepts and teachings of the present invention.

We claim as our invention:

1. A control desk for medical apparatus, said control desk comprising:
   an indicator panel (5),
   support means having a stationary control panel (2) and having an arrangement including guide means (11) supporting said indicator panel (5) in adjacent relation to said stationary control panel (2) for pivotal movement about a horizontal axis, so that the indicator panel (5) can be pivoted from a base position (I) into at least one operating position (II) where it is substantially angularly offset relative to said base position (I),
   said stationary control panel (2) having control elements (3, 4) carried thereby and operable to control said apparatus in response to operator manipulation while the operator is at an operator position proximate to said stationary control panel and while the operator has a direct view of the indicator panel (5) in the base position (I) thereof, and
   indicator elements (7 through 9) on said indicator panel (5) for providing optical information concerning the operation of said apparatus, which is useful while the operator is relatively remote from said stationary control panel (2),
   said indicator elements (7 through 9) being pivotally movable with said indicator panel (5) relative to said stationary control panel (2) so as to be more readily viewable from an operator position remote from said stationary control panel (2) in said one operating position (II) of said indicator panel (5) as compared with the case where the indicator panel (5) remains in said base position (I), the indicator panel (5) and the stationary control panel (2) having respective marginal edges which adjoin each other along said horizontal axis, and said indicator panel (5) having means cooperating with portions of said guide means (11) for preventing the displacement of the marginal edge of the indicator panel (5) away from said stationary control panel (2), so that the indicator panel (5) is movable only in a hinge-like fashion relative to said stationary control panel (2).

2. A control desk according to claim 1, characterized in that a cover hood (20) conforming to the pivot radius (r) is arranged on the indicator panel (5), said cover hood in the operating position (II) covering an opening (21) as the indicator panel (5) moves therefrom.

3. A control desk according to claim 1, characterized in that said guide means includes a guideway (11) is provided for the support of the indicator panel (5), said guideway having a slide engaged therewith.

4. A control desk according to claim 3, characterized in that the guideway (11) is arranged in the lateral wall (22) of the control desk (1).

5. A control desk according to claim 1, characterized in that the indicator panel (5) is arranged such that in said base position (I) the indicator panel (5) is substantially coplanar with the control panel (2) of the control desk (1).

6. A control desk according to claim 1, characterized in that the indicator panel (5) in its base position (I) is essentially horizontally arranged and can be pivoted into an operating position (II) situated at a substantial acute angle ($\alpha$) relative thereto.

7. A control desk according to claim 1, characterized in that a locking device (13 through 18) is present which supports the indicator panel (5) in several operating positions (II), each forming a different acute angle ($\alpha$) with said control panel (2).

8. A control desk according to claim 7, characterized in that the locking device (13 through 18) can be disengaged by means of pressing upon the indicator panel (5) in direction of the base position (arrow 19).

9. A control desk according to claim 7, characterized in that the locking device (13 through 18) contains a locking means (14) having several locking steps (13) and also a locking pawl (15) supported with the indicator panel (5), the pawl in each operating position (II) engaged with one of the locking steps (13).

10. A control desk according to claim 7, characterized in that the locking device (13 through 18) is present at both sides of the indicator panel (5) in the control desk (1).

11. A control desk according to claim 10, characterized in that the locking means (14) is integrated into the lateral wall (22) of the control desk (1).

12. A control desk for medical apparatus, in particular for an x-ray diagnostic apparatus, said control desk comprising:
   an indicator panel (5),
   support means (2, 22) having an arrangement including guide means (11) supporting said indicator panel (5) so that it can be pivoted from a base position (I) into a plurality of operating positions (II),
   control elements carried by said support means and operable to control said apparatus both in said base position (I) and in said operating positions (II),
   indicator elements (7 through 9) on said indicator panel (5) for providing optical information concerning the operation of said apparatus, said indicator elements (7 through 9) being movable with said indicator panel (5) so as to be more readily viewable from a given operator position in one of the operating positions (II) of said indicator panel (5) as compared with the base position (I) of said indicator panel (5), said arrangement further including a locking device (13 through 18) connected with said support means and with said indicator panel (5) for supporting the indicator panel (5) in each of said plurality of operating positions (II), said locking device comprising a locking means (14) having several locking steps (13) and also a locking pawl (15) with one end for engaging successively with the locking steps (13), and a spring bias (17) for urging said one end of said locking pawl (15) toward engagement with the locking steps (13), said indicator panel (5) having a carrier (16) supporting said locking pawl (15) for movement with said indicator panel (5), and in each operating position (II) of said indicator panel (5) engaging with one of the locking steps (13) with said one end thereof, with the aid of said spring bias (17), the arrangement being designed such that with a pivoting-out of the indicator panel (5) from its base position (I), the locking pawl (15) slides over and past the locking steps (13) and flips into an operative position after passing the last locking step (13''), so that the indicator panel (5) is then retained at each attained position as the panel is pivoted back in direction of the base position (arrow 19).

13. A control desk according to claim 12 with the arrangement being such that pressing upon the indicator panel (5) in the direction (arrow 19) corresponding to the pivoting of the indicator panel (5) from an attained position in the direction of the base position (arrow 19) ratchets the locking pawl (15) along the locking steps (13), characterized in that the locking pawl (15) is still engaged with the first locking step (13') when the indicator panel (5) is in the base position (I), and not until further pressing upon the indicator panel (5) does said locking pawl flip into a slide position (15'').

* * * * *